(12) United States Patent
Perez-Cruet et al.

(10) Patent No.: US 8,118,813 B2
(45) Date of Patent: Feb. 21, 2012

(54) BONE GRAFT DELIVERY SYSTEM FOR A VERTEBRAL INTERBODY DEVICE

(75) Inventors: Miguelangelo J. Perez-Cruet, Bloomfield, MI (US); John R. Pepper, Cheshire, CT (US); John A. Miller, Bloomfield Village, MI (US)

(73) Assignee: MI4Spine, LLC, Bloomfield Hills, MI (US)

( * ) Notice: Subject to any disclaimer, the term of this patent is extended or adjusted under 35 U.S.C. 154(b) by 1363 days.

(21) Appl. No.: 11/693,393

(22) Filed: Mar. 29, 2007

(65) Prior Publication Data

US 2008/0125856 A1 May 29, 2008

Related U.S. Application Data

(63) Continuation-in-part of application No. 11/605,641, filed on Nov. 29, 2006, now Pat. No. 7,803,159.

(51) Int. Cl.
*A61B 17/58* (2006.01)
*A61B 17/60* (2006.01)
*A61F 2/00* (2006.01)

(52) U.S. Cl. ........................................... 606/93
(58) Field of Classification Search .... 623/17.11–17.16; 606/99, 86 A, 114, 131, 914
See application file for complete search history.

(56) References Cited

U.S. PATENT DOCUMENTS

| 5,084,052 | A | 1/1992 | Jacobs |
| 6,066,153 | A * | 5/2000 | Lev ............................... 606/180 |
| 6,613,091 | B1 * | 9/2003 | Zdeblick et al. ........... 623/17.16 |
| 6,783,533 | B2 | 8/2004 | Green et al. |
| 2004/0140781 | A1* | 7/2004 | Craven et al. .................. 318/280 |
| 2004/0193170 | A1* | 9/2004 | Kemppainen et al. .......... 606/92 |
| 2005/0154460 | A1 | 7/2005 | Yundt |
| 2006/0149280 | A1 | 7/2006 | Harvie et al. |
| 2007/0225809 | A1* | 9/2007 | Ray ............................. 623/17.12 |

* cited by examiner

*Primary Examiner* — Thomas C. Barrett
*Assistant Examiner* — Sameh Boles
(74) *Attorney, Agent, or Firm* — John A. Miller; Miller IP Group, PLC

(57) ABSTRACT

A surgical delivery system that has particular application for providing bone graft material to an interbody device that restores disc space height during spinal fusion surgery. The bone graft delivery system includes a body portion and a shaft coupled thereto. An auger extends through a bore in the shaft and into the body portion. An end of the shaft opposite to the body portion is configured to be coupled to the interbody device, where the auger extends through a channel in the interbody device. Bone graft material is placed in a hopper coupled to the shaft, where the auger is manually or automatically rotated to deliver the bone graft material through the shaft and into the interbody device where it is dispersed into the disc space.

12 Claims, 4 Drawing Sheets

BONE GRAFT DELIVERY SYSTEM FOR A VERTEBRAL INTERBODY DEVICE

CROSS-REFERENCE TO RELATED APPLICATIONS

This application is a continuation-in-part application of U.S. patent application Ser. No. 11/605,641, filed Nov. 29, 2006, titled "Disc Space Preparation Device for Spinal Surgery."

BACKGROUND OF THE INVENTION

1. Field of the Invention

This invention relates generally to a bone graft delivery system for a vertebral interbody device and, more particularly, to a bone graft delivery system for a vertebral interbody device that includes an auger for delivering the bone graft material from a hopper to the interbody device to be disbursed within the vertebral disc space.

2. Discussion of the Related Art

The human spine includes a series of vertebrae interconnected by connective tissue referred to as disks that act as a cushion between the vertebrae. The disks allow for movement of the vertebrae so that the back can bend and rotate.

Spinal fusion is a surgical procedure that fuses two or more vertebrae together using bone grafts and/or other devices. Spinal fusion is a commonly performed procedure for the treatment of chronic neck and back pain refractory to non-operative treatments. Spinal fusion is used to stabilize or eliminate motion of vertebrae segments that may be unstable, i.e., move in an abnormal way, that may lead to pain and discomfort. Spinal fusion is typically performed to treat injuries to the vertebrae, degeneration of the spinal disks, abnormal spinal curvature and a weak or unstable spine.

In an attempt to preserve normal anatomical structures during spine surgery, minimally invasive surgical procedures have been devised. One such procedure involves the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

Spinal fusion generally requires a graft material, usually bone material, to fuse the vertebrae together. The bone graft material can be placed over the spine to fuse adjacent vertebrae together. Alternatively, a cage is positioned between the vertebrae being fused, and is filled with the graft material. This procedure is referred to as interbody fusion since it is between adjacent vertebra. The cage includes holes that allow the vertebra and the graft material to grow together to provide the fusion. The cage supports the weight of adjacent vertebra while the fusion is occurring through the cage. Alternatively, the bone graft material can be placed directly over or lateral to the spine, referred to as postero-lateral fusion. Typically the bone graft material is autogenous bone material taken from the patient, or allograft bone material harvested from cadavers. Synthetic bone materials can also be used as the graft material. Generally, the patient's own bone material offers the best fusion material and is the current "gold standard".

Spinal instrumentation is then performed to immobilize the vertebral segments where the bone is placed. Similar to the function of wearing a cast or brace after breaking a long bone, spinal instrumentation allows for immobilization, which promotes bone fusion. One of the most common forms of spinal instrumentation is a pedicle screw and rod construct. The rods, which span adjacent vertebra, are mounted to the vertebra using pedicle screws that are threaded through the pedicles of each vertebra and into the vertebral body. Accurate placement of the pedicle screws relative to the vertebral pedicle is very important to prevent injury to nerves or spinal cord. Typically, fluoroscopy is used to ensure that the pedicle screws are properly oriented relative to the pedicle.

During spinal fusion surgical procedures, it is necessary to completely remove the disc and clean out the disc space between the vertebra being fused. Particularly, it is necessary to remove as much of the disc material as possible between the vertebra so that the graft material that will be provided between the vertebra for the fusion provides a good bone-to-bone adhesion. Any remaining disc material that is not removed reduces the chance that the graft material will provide the bone graft adhesion necessary for a satisfactory fusion process.

Currently, various surgical devices are used in the art to remove the disc material for both minimally invasive and open spinal fusion procedures. For minimally invasive spinal surgery, a cutting device, such as a pituitary rongeur, is used to remove the disc material. The pituitary rongeur is a mechanical device including a "cup end" that cuts and scoops out the disc material to remove it in a mechanical operation. Manipulating the cup end of the pituitary rongeur is relatively cumbersome in that it is limited in its ability to clear the disc space around corners and other "guarded" areas proximate to the vertebrae. Further, because the pituitary rongeur is a mechanical device, it is limited in its ability to protect sensitive parts of the vertebrae, such as spinal nerves running through the disc space.

SUMMARY OF THE INVENTION

In accordance with the teachings of the present invention, a surgical delivery system is disclosed that has particular application for providing bone graft material to an interbody device that restores disc space height during spinal fusion surgery. The delivery system includes a body portion and a shaft coupled thereto. An auger extends through a bore in the shaft and into the body portion. An end of the shaft opposite to the body portion is configured to be coupled to the interbody device, where the auger extends through a channel in the interbody device. Bone graft material is placed in a hopper coupled to the shaft, where the auger is manually or automatically rotated to deliver the bone graft material through the shaft and into the interbody device where it is dispersed into the disc space.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a bone graft delivery system is merely exemplary in nature, and is in no way intended to limit the invention or its applications or uses. For example, the bone graft delivery system of the invention has particular application for delivering bone graft material to an interbody device positioned between adjacent vertebra being fused together during spinal fusion surgery. However, as will be appreciated by those skilled in the art, the bone graft delivery system of the invention may have application for other surgical and non-surgical operations.

Figure 1:
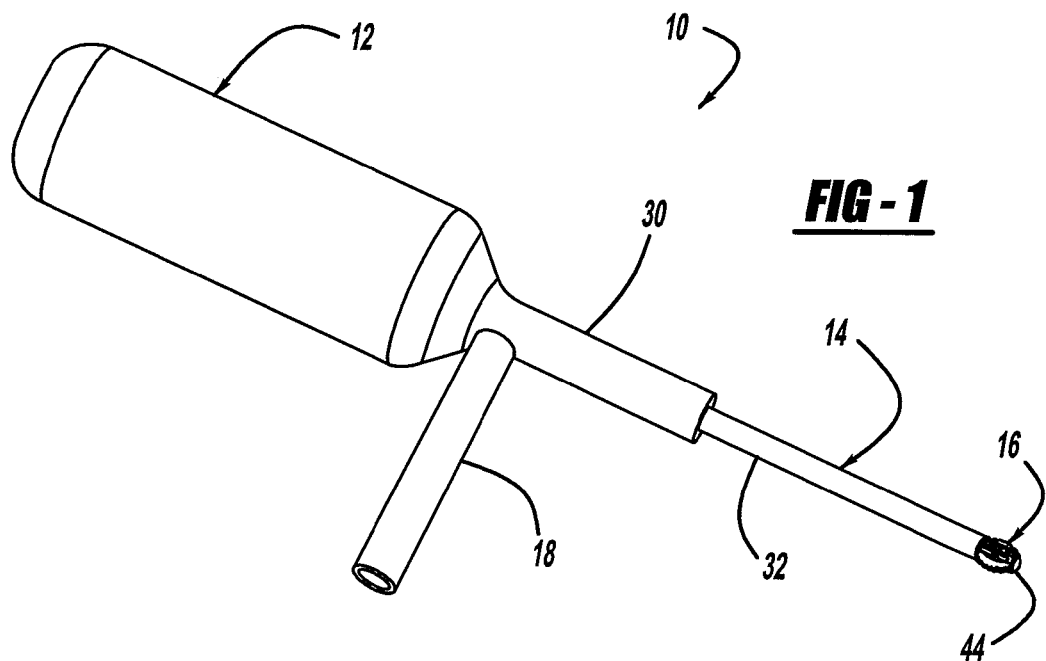
FIG. 1 is a perspective view of a disc space preparation device for spinal fusion surgery, according to an embodiment of the present invention.
Figure 2:
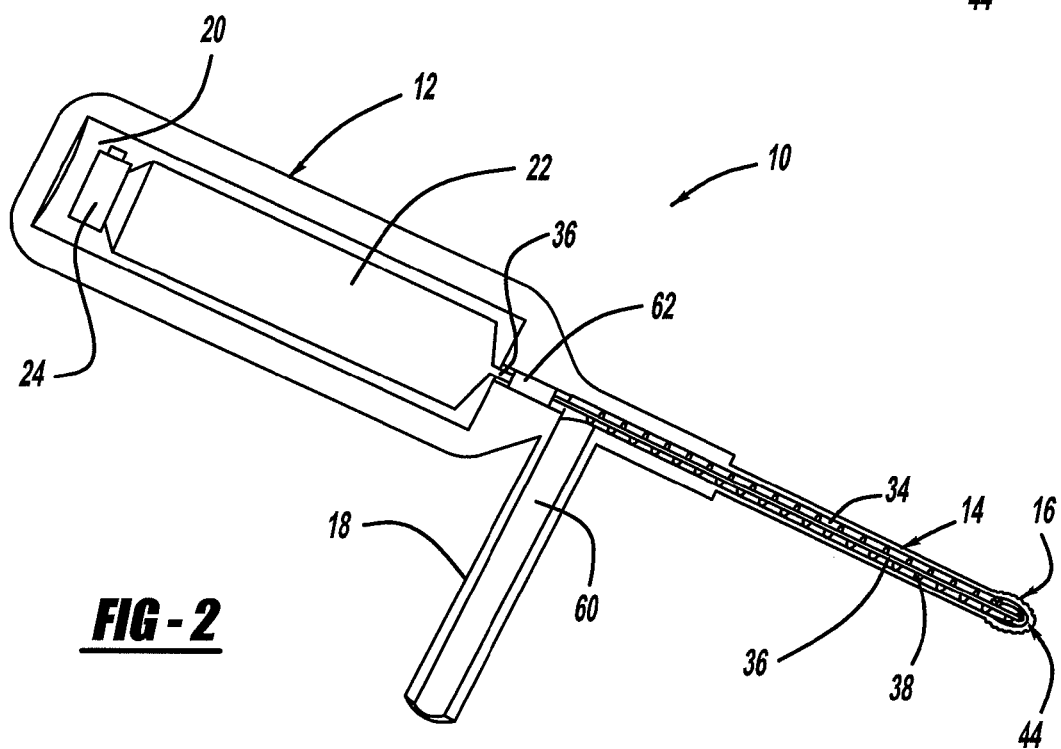
FIG. 2 is a broken-away perspective view of the disc space preparation device shown in FIG. 1.

FIG. 1 is a perspective view and FIG. 2 is a cut-away, perspective view of a disc space preparation device 10, according to an embodiment of the present invention. The disc space preparation device 10 includes a body portion 12, an elongated neck portion 14 attached to the body portion 12, an open cutting head portion 16 attached to the neck portion 14 opposite to the body portion 12, and a suction port 18. The body portion 12 includes an internal chamber 20 in which is mounted an electric motor 22. The electric motor 22 can be a DC motor powered by batteries 24 or an AC motor powered by an electrical power cord (not shown). Further, the motor 22 can be a variable speed motor. Alternately, the motor 22 can be eliminated and the device 10 can be pneumatic or vacuum driven.

In this non-limiting embodiment, the elongated neck portion 14 has a step configuration including a wider diameter portion 30 and a narrow diameter portion 32, where the wider portion 30 provides increased stiffness. The neck portion 14 further includes a neck chamber 34 that is in fluid communication with the open cutting head portion 16. A shaft 36 is coupled to the motor 22, and extends through the neck chamber 34. The shaft 36 includes a screw or auger 38 for reasons that will become apparent from the discussion below. When the motor 22 is turned on, the shaft 36 and the auger 38 rotate. In one non-limiting embodiment, the auger 38 has a pitch-to-diameter ratio of about 1:1. Further, the neck portion 14 can be made of a suitable low friction material, such as stainless steel, to support the rotation of the auger 38.

Figure 3:
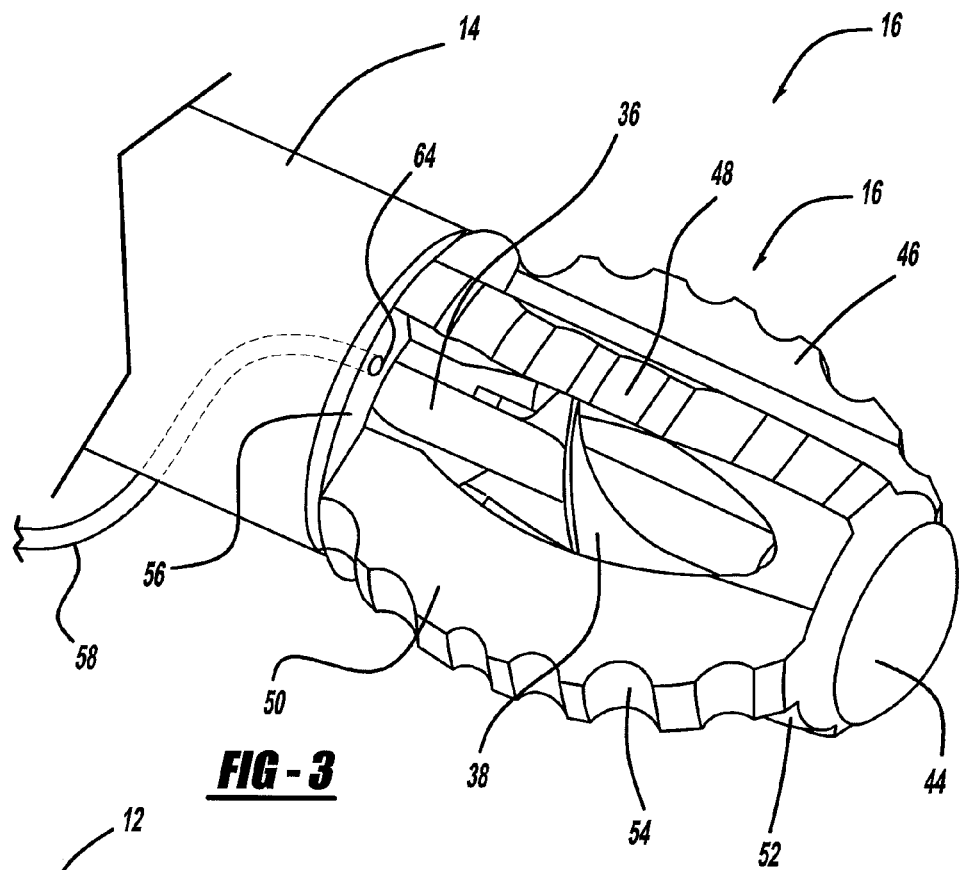
FIG. 3 is a perspective view of a head portion of the disc space preparation device shown in FIG. 1.

FIG. 3 is a perspective view of the head portion 16. The head portion 16 includes an end cap 44 in which an end of the shaft 36 can be rotatably mounted by bearings or the like. The end portion 16 also includes four symmetrically disposed cutting blades 46, 48, 50 and 52 each having a serrated cutting edge 54, although the cutting edge does not need to be serrated for other embodiments. The head portion 16 is open to the chamber 34 between the cutting blades 46-52, as shown. The head portion 16 is mounted to the neck portion 14 so that it rotates relative thereto in any suitable manner. The cutting blades 46-52 can be made of any suitable material, such as stainless steel. In this embodiment, the cutting blades 46-52 have a general arced configuration. However, this is by way of a non-limiting embodiment, in that any cutting blade configuration suitable for the purposes described herein can be employed.

During the disc preparation part of spinal fusion surgery, the surgeon will grasp the body portion 12, and position the cutting blades 46-52 within the disc space through an incision in the patient. The surgeon then causes the end portion 16 to rotate the cutting blades 46-52 to cut away the disc material. The cutting blades 46-52 shield the auger 38 so that it does not contact the tissue. The neck portion 14 and the cutting head portion 16 have a size that is suitable for minimally invasive spinal surgical procedures. In one non-limiting embodiment, the neck portion 14 is about 9 inches long and the narrow portion 32 has a diameter of about 8 mm. As the cutting blades 46-52 cut away the disc material, the disc material will fall into the open spaces between the cutting blades 46-52. As the shaft 36 rotates, the auger 38 will draw away the cut disc material through the chamber 34 towards the motor 22. The head portion 16 and the auger 38 can be rotated in opposite directions for maximum efficiency. If the motor 22 is variable, the cutting blades 46-52 and the auger 38 can be rotated at different speeds. The stepped configuration of the neck portion 14 allows for more material to be collected in the neck chamber 34 opposite to the head portion 16.

In this non-limiting embodiment, the diameter of the auger 38 is slightly less than the diameter of the chamber 34 so that the auger nearly completely fills the chamber 34 and is able to easily rotate therein. An annular shredding member 56 is provided between the head portion 16 and the neck portion 14. The shredding member 56 has a relatively sharp cutting edge that acts to shred larger pieces of material that have been cut and are being drawn away by the auger 38 so that they can easily travel through the chamber 34. An edge of the auger 38 can also be equipped with a scraper (not shown) to prevent clogging within the neck chamber 34. Further, the auger 38 can include teeth (not shown) to reduce the size of the material being cut away. Also, an irrigation line 58 can be provided that emits water or some other lubricant into the head portion 16 through an orifice 64 so that the water is drawn up the neck portion 14 by the auger 38 and acts to lubricate the chamber 34 and help draw the material out of the neck portion 14.

The suction port 18 includes a channel 60 that is in fluid communication with the chamber 34. A suction line (not shown) is coupled to the suction port 18 and sucks the cut away material out of the chamber 34 using a vacuum pump (not shown). A seal 62 is provided around the shaft 36 between the motor chamber 20 and the chamber 34 to prevent the material that is cut away from entering the body chamber 20. In this manner, the device 10 can be used to accurately and quickly remove the disc material between the vertebrae being fused during the surgical procedure, especially around the edges and contours of the vertebra.

Figure 4:
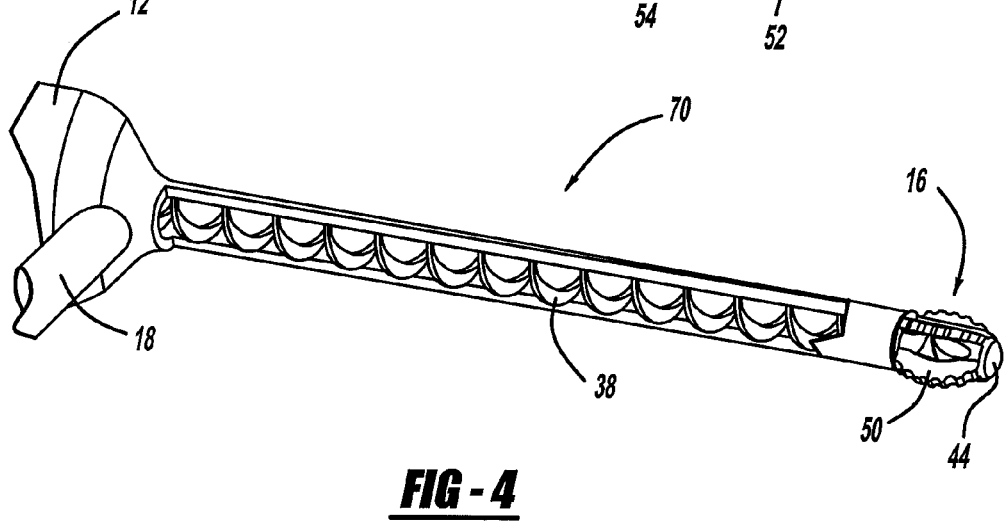
FIG. 4 is a broken-away perspective view of a disc space preparation device including an auger without a center shaft, according to another embodiment of the present invention.

FIG. 4 is a cut-away perspective view of a disc space preparation device 70, according to another embodiment of the present invention, where like components to the disc space preparation device 10 are identified by the same reference numeral. In this embodiment, the shaft 36 has been eliminated where the auger 38 alone rotates within the chamber 34. This configuration will reduce the cost and weight of the device 70.

Figure 5:
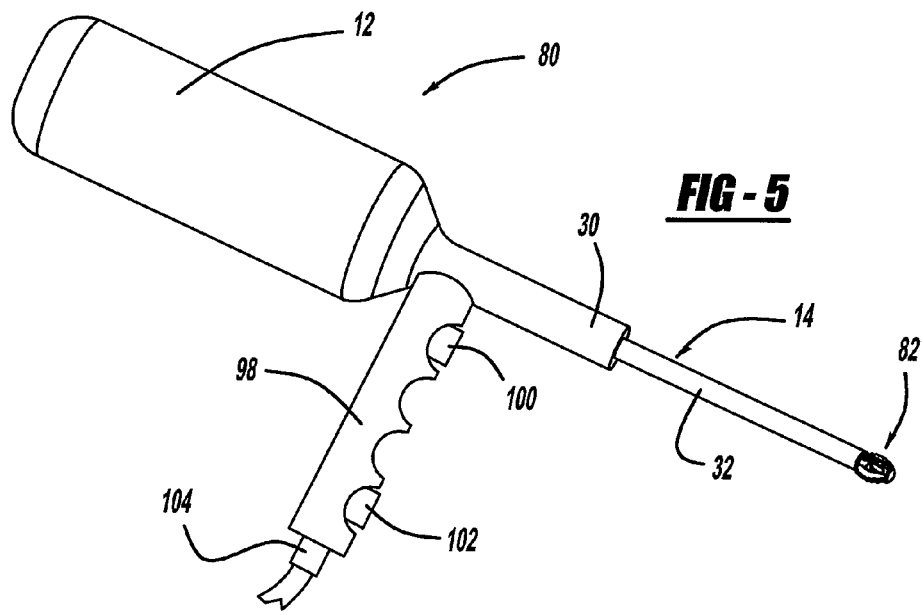
FIG. 5 is a perspective view of a disc space preparation device employing a pistol grip and a rotating cutting head portion, according to another embodiment of the present invention.
Figure 6:
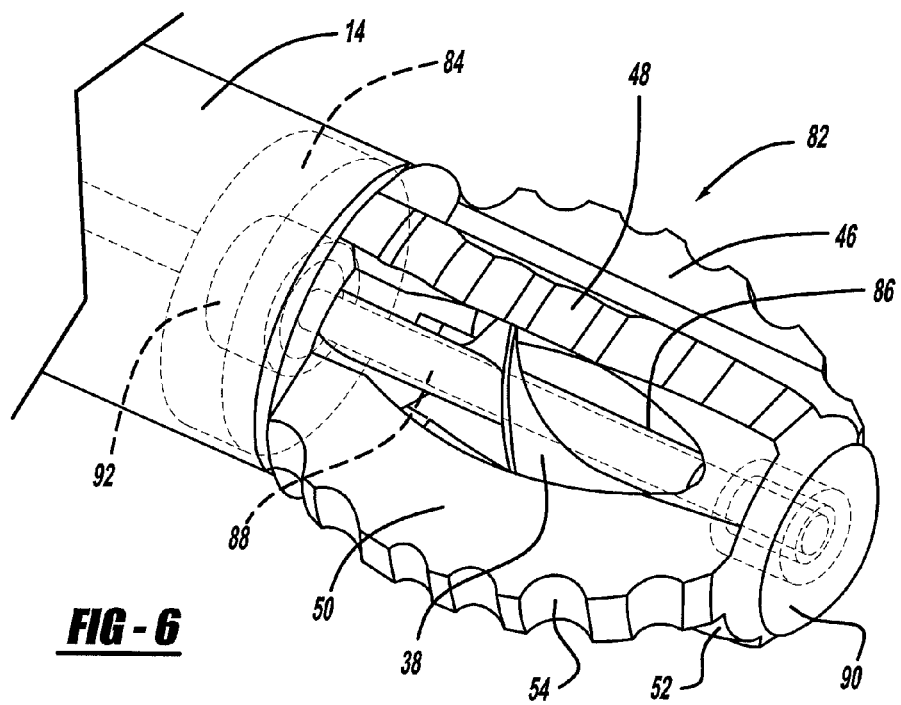
FIG. 6 is a perspective view of the head portion of the device shown in FIG. 5.

FIG. 5 is a perspective view of a disc space preparation device 80, according to another embodiment of the present invention, where like elements to the disc space preparation device 10 are identified by the same reference numeral. The disc space preparation device 80 includes a head portion 82 that is rotatable relative to the neck portion 14 on bearings 84 in a manner that would be well understood to those skilled in the art. A close-up view of the head portion 82 is shown in FIG. 6. The device 80 includes an outer shaft 86 and an inner shaft 88 where the shafts 86 and 88 are concentric. The shaft 86 includes an internal bore, where the shaft 88 is easily rotatable therein. The auger 38 is attached to the outer shaft 86. The inner shaft 88 is rigidly coupled to an end cap 90 of the head portion 82 so that when the inner shaft 88 rotates, the head portion 82 rotates on the bearings 84. The outer shaft 86 rotates within the chamber 34 in the same direction or an opposite direction to the inner shaft 88. The rotating head portion 82 causes the blades 46-52 to cut the disc material, and the rotating auger 38 draws the cut disc material away as discussed above.

The shafts 86 and 88 are coupled to a gear system 92 that causes the shafts 86 and 88 to rotate in the same or opposite directions. The gear system 92 can be any suitable gear system for the purposes described herein, such as a planetary gear system.

The device 80 also includes a pistol grip 98 rigidly coupled to the neck portion 14 that allows the surgeon to easily hold on to the device 80. The pistol grip 98 includes an on/off button 100 that can be pressed to turn the device 80 on and be released to turn the device 80 off. A second button 102 can be provided that allows the surgeon to stop the inner shaft 86 from rotating and only allow the outer shaft 86 to rotate for intricate manual cutting where the rotating head portion 82 may be to risky for cutting near a nerve. One skilled in the art would readily understand how to configure the gear system 92 to provide this operation. Particularly, the surgeon can hold the button 100 so that both of the shafts 86 and 88 rotate, and can selectively press the second button 102 when the surgeon wants the head portion 82 to stop rotating, but the outer shaft 86 to continue to rotate. The pistol grip 98 includes an internal chamber in fluid communication with the chamber 34 and a suction port 104 so that the cut-away material can be sucked out of the device 80, as discussed above.

Figure 7:
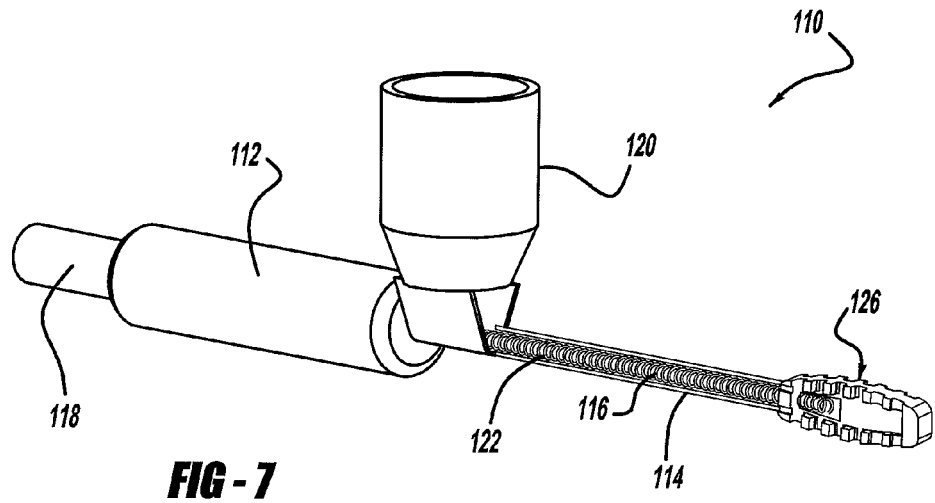
FIG. 7 is a perspective view of a bone graft delivery system for delivering bone graft material to an interbody device positioned with a disc space, according to an embodiment of the present invention.

The concept of the invention discussed above can also be used as a delivery system to deliver material to the disc space between two vertebra, or deliver other materials to other surgical sites. FIG. 7 is a perspective view of a bone graft delivery system 110 including a body portion 112 and a shaft 114 extending therefrom, according to another embodiment of the present invention. An auger 116 extends through a bore 122 in the shaft 114, and into the body portion 112. The auger 116 can be any auger suitable for the purposes described herein, such as those discussed above, or other suitable augers.

In this embodiment, rotation of the auger 116 is manually controlled by an auger control mechanism 118; however, an electrically driven auger is within the scope of the present invention. The auger control mechanism 118 is mechanically attached to the auger 116 within the body portion 112 in any suitable manner so that rotation of the control mechanism 118 causes the auger 116 to rotate, both forward and backward.

However, in alternate embodiments, it is possible to include a low speed motor or variable speed motor within the housing 112 to drive the auger 116. If the system 110 includes an electric motor, it can also include the pistol grip 98 mounted to the body portion 112 and having the on/off button 100 to start and stop the rotation of the auger 116. A hopper 120, or other suitable storage device, is open to the bore 122 in the shaft 114. The hopper 120 is filled with the bone graft material, and as the auger 116 rotates, the bone graft material is delivered from the hopper 120 down the shaft 114.

U.S. patent application Ser. No. 11/623,356, filed Jan. 16, 2007, titled "Minimally Invasive Interbody Device", assigned to the Assignee of this application and herein incorporated by reference, discloses an interbody device that is inserted between two vertebra to restore disc height. In one non-limiting embodiment, the bone graft delivery system 110 is used to deliver the bone graft material to an interbody device 126 of the type disclosed in the '356 application.

Figure 8:
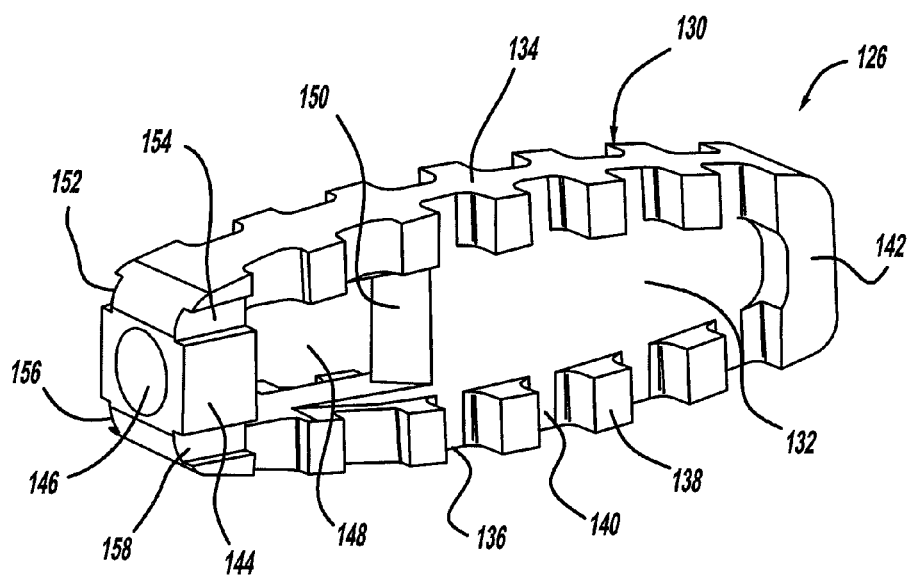
FIG. 8 is a perspective view of the interbody device removed from the delivery system.

FIG. 8 is a perspective view of the interbody device 126 separated from the delivery system 110, and is the same interbody device shown and described in FIG. 10 of the '356 application. However, it is stressed that the interbody device 126 as shown and described is by way of a non-limiting example in that other interbody device designs can be employed and other types of devices can be used within the scope of the present invention.

The interbody device 126 includes a perimeter portion 130 and a center plate 132 that are an integral body. The perimeter portion 130 includes opposing spines 134 and 136 having ribs 138 extending therefrom. The ribs 138 define spaces 140 therebetween along the length of the spines 134 and 136. The perimeter portion 130 also includes a first end piece 142 and a second end piece 144, where a channel extends through the end piece 144. The center plate 132 includes an opening 148 in communication with the channel 146 to facilitate distribution of the bone graft material. The center plate 132 includes a ridge 150 extending into the opening 148, where the ridge 140 helps to distribute the bone graft material on both sides of the center plate 132 within the disc space. The end piece 144 also includes a first set of two opposing slots 152 and 154 on opposite sides of the end piece 144 and a second set of two opposing slots 156 and 158 on opposite sides of the end piece 144, as shown.

The shaft 114 includes suitable fingers (not shown) that are slid down the slots 152-158 to grasp the interbody device 126 when the auger 116 is extended through the channel 146 and into the opening 148. Any other suitable attachment mechanism can be used to secure the shaft 114 to the interbody device in other embodiments.

In the embodiment described above, the auger 116 extends into the opening 148 of the interbody device 126. In alternate embodiment, the auger 116 does not extend into the opening 148 of the interbody device 126, but stops within the channel 146 or before the interbody device 126. A tube (not shown) can be provided to deliver the bone graft material from the end of the auger 116 to the opening 148.

As discussed in the '356 application, the interbody device 126 is rotated when it is inserted into the disc space so that it is turned from a flat configuration to an upright configuration to provide a force to separate the discs. The bone graft delivery system 110 can be used to provide the rotation for this purpose.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A surgical device comprising: a body portion; an elongated shaft including a shaft chamber coupled to the body portion; an auger extending through the shaft chamber, said auger being rotatable to deliver a material from one end of the shaft to an opposite end of the shaft; and an interbody member rigidly and detachably mounted to the shaft opposite to the body portion, said interbody member being configured to remain in a human body after a surgical procedure, said auger being rotatable relative to the shaft and the interbody member to deliver the material to the interbody member, where the auger extends through a channel in the interbody member, wherein the interbody member includes a perimeter portion having spaced apart elongated members extending along a length of the perimeter portion and opposing end pieces coupled to the elongated members, wherein one of the end pieces includes the channel extending therethrough.

2. The device according to claim 1 further comprising an auger control mechanism mounted to the body portion, said auger control mechanism being coupled to the auger and being operable to manually turn the auger.

3. The device according to claim 1 further comprising a motor positioned within the body portion, said motor being operable to rotate the auger.

4. The device according to claim 3 further comprising a pistol grip mounted to the body portion, said pistol grip including an on/off button for the motor.

5. The device according to claim 1 further comprising a hopper mounted to the shaft and being open to the shaft chamber, said hopper being operable to hold a material that is provided to the shaft chamber to be delivered to an end of the shaft opposite to the body portion by the auger.

6. The device according to claim 5 wherein the material is bone graft material.

7. The device according to claim 6 wherein the device is dimensionally sized to deliver the bone graft material to a disc space between vertebra.

8. The device according to claim 1 wherein said perimeter portion further including a plate member positioned within the perimeter portion, said plate member including an opening proximate the channel.

9. The device according to claim 8 wherein the auger extends into the opening.

10. A system for delivering bone graft material to a disc space between adjacent vertebra, said system comprising:
a body portion;
an elongated shaft including a shaft chamber coupled to the body portion;
a hopper for holding the bone graft material and being open to the shaft chamber;
an auger extending through the shaft chamber; and
an interbody device rigidly and detachably coupled to an end of the shaft opposite to the body portion, said interbody device being configured to remain in a human body after a surgical procedure, said auger being rotatable relative to the shaft and the interbody device to deliver the bone graft material from the hopper to the interbody device to be dispersed within the disc space, where the interbody device includes a channel, said auger extending into the channel, and where the interbody member includes a perimeter portion having spaced apart elongated members extending along a length of the perimeter portion and opposing end pieces coupled to the elongated members, wherein one of the end pieces includes the channel extending therethrough, said perimeter portion further including a plate member positioned within the perimeter portion, said plate member including an opening proximate the channel.

11. The system according to claim 10 further comprising an auger control mechanism mounted to the body portion, said auger control mechanism being coupled to the auger and being operable to manually turn the auger.

12. A system for delivering bone graft material to a disc space between adjacent vertebra, said system comprising: a container for holding the bone graft material; a rotatable auger for delivering the bone graft material from the container to the disc space; a shaft including a shaft channel, said auger extending through the shaft channel and said container being attached to the shaft and open to the shaft channel; and an interbody device mounted to an end of the shaft, said interbody device including a device channel, said auger extending into the device channel, wherein the interbody device includes a perimeter portion having spaced apart elongated members extending along a length of the perimeter portion and opposing end pieces coupled to the elongated members, wherein one of the end pieces includes the device channel extending therethrough.

* * * * *